(12) United States Patent
McNair

(10) Patent No.: US 11,694,814 B1
(45) Date of Patent: *Jul. 4, 2023

(54) DETERMINING PATIENT CONDITION FROM UNSTRUCTURED TEXT DATA

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/942,066

(22) Filed: Jul. 29, 2020

Related U.S. Application Data

(63) Continuation of application No. 14/960,249, filed on Dec. 4, 2015, now Pat. No. 10,770,184.

(60) Provisional application No. 62/087,514, filed on Dec. 4, 2014.

(51) Int. Cl.
*G16H 50/50* (2018.01)
*G16H 10/60* (2018.01)

(52) U.S. Cl.
CPC ............ *G16H 50/50* (2018.01); *G16H 10/60* (2018.01)

(58) Field of Classification Search
CPC .... G16H 10/60; G06F 16/367; G06F 17/2705
See application file for complete search history.

(56) References Cited

U.S. PATENT DOCUMENTS

2015/0227691 A1* 8/2015 Bhattacharya ........... G06N 7/01
705/3

FOREIGN PATENT DOCUMENTS

CN 105095229 A * 11/2015 ....... G06F 17/30734

OTHER PUBLICATIONS

Roberts, Margaret et al. Structural Topic Models for Open-Ended Survey Responses. American Journal; of Political Science, vol. 58, Issue 4, first published: Mar. 6, 2014. pp. 1064-1082. http://scholar.harvard.edu/files/dtingley/files/topicmodelsopenendedexperiments.pdf (Year: 2014).*
Wu, Cai et al. EM Clustering Analysis of Diabetes Patients Basic Diagnosis Index. AMIA Annual Symposium Proceedings Archive. 2005: 1158. (Year: 2005).*

(Continued)

*Primary Examiner* — Linh Giang Le
(74) *Attorney, Agent, or Firm* — Invoke

(57) ABSTRACT

Systems, methods and computer-readable media are provided for determining the likelihood of a presence or absence of one or more patient conditions based on unstructured text data from the electronic health records, which may accrue during the routine provisioning of care services. In particular, embodiments described herein use structural topic modeling (STM) to assess the textual information as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the patient.

20 Claims, 18 Drawing Sheets

(56) References Cited

OTHER PUBLICATIONS

Roberts et al., "Structural Topic Models for Open-Ended Survey Responses", American Journal of Political Science, vol. 58, No. 4, Available online at: <http://scholar.harvard.edu/files/dtingley/files/topicmodelsopenendedexperiments.pdf>, Oct. 2014, pp. 1064-1082.

Wu et al., "EM Clustering Analysis of Diabetes Patients Basic Diagnosis Index", AMIA Annual Symposium Proceedings, 2005, p. 1158.

* cited by examiner

| 1 | meta_foley | text |
|---|---|---|
| 2 | Y | "30 Y.O. WOMAN ADM [3145-5-15] WITH PMH OF BORDERLINE PERSONALITY D/O, PTSD, ANXIETY AND DE |
| 3 | Y | "44 YO DEVELOPMENTALLY DELAYED MALE S/P EXP. LAP, LOA, TRANSVERSE/LEFT COLECTOMY, COLOPRO |
| 4 | Y | "58 Y.O. WOMAN WITH SMALL LUNG CELL CA WITH LIVER AND SPINE METS DEV. 2 MONTHS AGO, WITH LG |
| 5 | Y | "58 YR OLD MALE ADMITTED FROM 11[HOSPITAL WARD NAME1] SMALL CELL LUNG CA PRESENTING WITH |
| 6 | Y | "62 Y.O. MAN ADM[11-6] WITH PMH OF MS, DEMENTIA, GERD, OSTEOMYELITIS R/T SPINAL DECUB, URIN |
| 7 | Y | "73 YEAR-OLD NURSING HOME RESIDENT ADMITTED WITH FEVER, CHANGE MS, HYPOTENSION, DECREAS |
| 8 | Y | "73 YO MALE S/P UNWITNESSED FALL FROM ROOF 2 [1-17] STORIES ONTO CONCRETE. PT FOUND BY N |
| 9 | Y | "99 TEMP, 70-80S AFIB, SBP 100-119/50S, LOPRESSOR DOSE DECREASED 7.5 TO 5MG IV Q 6 AND 1200 PM L |
| 10 | Y | "99.6 TEMP, 70-80S AFIB, SBP 100-119/50S, LOPRESSOR DOSE DECREASED 7.5 TO 5 MG IV Q 6 AND 1200 PN |

...

| 173 | N | "RESP: RR 22, LUNGS COARSE PRIOR TO SX AND CLEAR IN UPPER LOBES DIM IN BASED AFTER SX. CV: B/ |
| 174 | N | "RESPIRATORY: MOST OF AM RR 28-30. VISIBLY DYSPNIC. O2 SATS 96-98% ON 5l NC. RALES THROUGH-OU |
| 175 | N | "RESPINDS TO VOICE. FOLLOWING COMMANDS, PERRLA 2MM. MAE ON BED. TMAX 102, TEAM AWARE, PT. |
| 176 | N | "S: 'CAN'T I JUST HAVE SOMETHING TO MAKE ME GO[DOCTOR LAST NAME 8]'?' NEURO: PT IS A&OX3, VER |
| 177 | N | "S: 'OH, I'M IN SO MUCH PAIN', 'IT HURTS.' O: SEE CAREVUE FOR COMPLETE ASSESSMENT DATA. NEURO |
| 178 | N | "C/O PAIN. O: SMALL INTERMITTENT DOESES OF MORPHINE, RESPONDS VERBALLY, MOVES ALL EXTREMI |
| 179 | N | "S: 'GIMME SOMETHING TO HELP ME [DOCTOR LAST NAME 8]'. O: SEE CAREVIEW FOR OBJECTIVE DATA |
| 180 | N | "S-'LOOK LIKE I GOING TO BE HERE FOR FEW DAYS.' O-MS:A/O/X3. ORIGINALLY FROM POLAND BUT SPEAK |

FIG. 3A.

TOPIC 1:
insulin, stabl, clear, gtt, status, med, neuro, sat, need, resp, replet, urin, soft, base, activ, orient, lab, glucos, hct, pain

TOPIC 2:
place, continu, foley, name, resp, last, urin, plan, monitor, line, admiss, pain, gtt, sinc, arriv, famili, bolus, neuro, report, fluid

TOPIC 3:
clear, resp, remain, skin, plan, neuro, note, yellow, urin, continu, pain, shift, chang, cchr, deni, follow, command, today, sound, monitor

TOPIC 4:
home, skin, pain, name, intact, sat, extrem, clear, urin, neuro, need, foley, receiv, plan, care, full, resp, back, continu, cough

TOPIC 5:
name, order, given, blood, neuro, plan, clear, done, left, right, last, agit, hospit, note, urin, good, swallow, follow, back, present

TOPIC 6:
pain, given, sbp, foley, effect, cough, urin, ptt, abd, plan, continu, site, monitor, clear, awar, mae, name, wean, afib, good

TOPIC 7:
cont, last, name, follow, hct, neuro, goal, even, lab, note, social, today, pain, based, heme, famili, cchr, plan, abd, clear

TOPIC 8:
name, lasix, last, today, cont, good, resp, well, neuro, monitor, doctor, start, day, lopressor, abd, see, clear, med, neg, care

TOPIC 9:
given, place, sat, sinc, current, state, mask, anxieti, breath, ativan, bipap, use, take, sbp, back, son, pull, home, bed, support

TOPIC 10:
Pain, drain, remain, continu, fentanyl, hrs, monitor, urin, fluid, abg, follow, abd, scant, chang, soft, map, foley, receiv, brown, last

|  | True Positive | True Negative |
|---|---|---|
| Predict Positive | 86 | 7 |
| Predict Negative | 4 | 83 |

SENSITIVITY = 96%
SPECIFICITY = 92%

*FIG. 7B.*

```
###########################################################################

# CERDSM - structural topic model mining; foley catheter vs. no foley in-patient population

##################################################################### library(stm)
library(SnoballC)
library(tm)
library(proxy)
library(smdc)

gu <- read.csv(file="c:/0_cerdsm/0_DAAKOS/0_caredecisions_dynamic_caresets/questionnaire_synth/
dsm_stm_foley.csv",
        header=TRUE, sep=",", quote="\"", dec=".", fill=TRUE, comment.char="",
        colClasses=c("factor","character"))

# stopword removal, word stemming, lowercase transformation, punctuation/whitespace stripping, etc.
# if care decision topic (meta factor) is a string that appears in text corpus, then mask it with custom stopwords
table
processed <- textProcessor(gu$text, metadata=gu, verbose=FALSE,
  lowercase=TRUE, removestopwords=TRUE, removenumbers=TRUE,
  removepunctuation=TRUE, stem=TRUE, sparselevel=0.99, language="en")

# create structure and index corpus for STM model; verify no-missingness
# out object documents, vocab, meta (81 docs; 1,014 distinct words // 180 docs; 1,662 distinct words)
out <- prepDocuments(processed$documents, processed$vocab, processed$meta,
  lower.thresh=1, upper.thresh=Inf, subsample=NULL, verbose=FALSE)
str(out)

# fit 10-topic model via 75 EM iterations
guPrevFit <- stm(out$documents, out$vocab, K=10,
  prevalence =~ meta_foley, max.em.its=75,
  data=out$meta, seed=1239)

# assess whether adequate convergence is achieved in 75 iterations
plot(guPrevFit$convergence$bound, type="l", ylab="Approximate Objective", main="Convergence", lwd=3,
col="red")

# select best 10-topic model from 20 runs, each run having 75 Expectation-Maximization iterations
guSelect <- selectModel(out$documents, out$vocab, K=10,
  prevalence =~ meta_foley, max.em.its=75,
  data=out$meta, runs=20, seed=1239)

# plot the 4 best models' semantic coherence for the 10 extracted topics
plotModels(guSelect)

# and assign the model with best performance for further use in classification of other texts
# choose the first model (numeral pt icons: least-negative avg semantic coherence; highest avg exclusivity)
guPrevFit <- guSelect$runout[[1]]

.
.
.

Continues in FIG. 9B
```

*FIG. 9A*

Continues FROM FIG. 9A

. . .

```
# inspect topics pairwise
labelTopics(guPrevFit, c(1:2))

# display top-20 words by frequency, one row per topic
plot.STM(guPrevFit, type="labels")

# 81-doc model topics 4, 5, and 8 are associated with foley catheter; 5 is strongest association
# 81-doc model topics 1, 3, 6, and 7 are associated w/ no foley; 3 is strongest
# 180-doc model topics 2 and 6 are associated with foley catheter; 6 is stronger association
# 180-doc model topics 3, 7, and 8 are associated w/ no foley; 8 is strongest
# thoughts4 <- findThoughts(guPrevFit, texts={record}, n=2, topics=4)$docs[[1]]

# calculate and plot effects
prep <- estimateEffect(1:10 ~ meta_foley, guPrevFit,
  meta=gu, uncertainty="Global")

# level="Y" are those topics that are associated with foley; level="N" assoc w/ no foley
# 95%LCI error bars not touching 0.00 are statistically significant
plot.estimateEffect(prep, covariate="meta_foley", model=guPrevFit,
  method="pointestimate")

plot.estimateEffect(prep, covariate="meta_foley", model=guPrevFit,
  method="difference", cov.value1="N",cov.value2="Y")

# 2-topic wordclouds for topic pairs that distinguish between presence or absence of meta factor
plot.STM(guPrevFit, type="perspectives", topics=c(2,3))
plot.STM(guPrevFit, type="perspectives", topics=c(2,7))
plot.STM(guPrevFit, type="perspectives", topics=c(2,8))
plot.STM(guPrevFit, type="perspectives", topics=c(6,3))
plot.STM(guPrevFit, type="perspectives", topics=c(6,7))
plot.STM(guPrevFit, type="perspectives", topics=c(6,8))

# display topic quality metrics
guTopicQual <- topicQuality(model=guPrevFit, documents=out$documents)
guTopicQual identify representative documents in target cluster(s)
foley.clust <- findThoughts(guPrevFit, texts=out$documents, topics=c(2,6), n=10)
foley.clust$index[[1]]
foley.clust$index[[2]]

# get at least 2 notes from test case and perform pre-processing
test <- read.csv(file="c:/0_cerdsm/0_DAAKOS/0_caredecisions_dynamic_caresets/questionnaire_synth/test.csv",
        header=TRUE, sep=",", quote="\"", dec=".", fill=TRUE, comment.char="",
        colClasses=c("factor","character"))
```

. . .

Continues in FIG. 9C

FIG. 9B

Continues FROM FIG. 9B

```
test.processed <- textProcessor(test$text, metadata=test)

test.out <- prepDocuments(test.processed$documents, test.processed$vocab, test.processed$meta,
  lower.thresh=1, upper.thresh=Inf, subsample=NULL, verbose=FALSE)
str(test.out)

# determine fit to existing model
subset gu to select just those exemplars of each of the Y/N meta factor
len1 <- length(foley.clust$index[[1]])

doc1 <- data.frame(gu$text[sort(foley.clust$index[[1]])])
# doc1 <- data.frame(c("This is an example text.", "This another one."))
# doc1 <- data.frame(processed$vocab)
ds1 <- DataframeSource(doc1)
ds1.corpus <- VCorpus(ds1)
dtm1 <- DocumentTermMatrix(ds1.corpus, control=list(weighting=function(x)
                weightTfIdf(x, normalize=FALSE), stopwords=TRUE))
docMatrix1 <- t(as.matrix(DocumentTermMatrix(ds1.corpus)))

doc2 <- data.frame(test$text)
# doc2 <- data.frame(c("This is our text.", "This a peculiar one."))
# doc2 <- data.frame(test.processed$vocab)
ds2 <- DataframeSource(doc2)
ds2.corpus <- VCorpus(ds2)
dtm2 <- DocumentTermMatrix(ds2.corpus, control=list(weighting=function(x)
                weightTfIdf(x, normalize=FALSE), stopwords=TRUE))
docMatrix2 <- t(as.matrix(DocumentTermMatrix(ds2.corpus)))

# smdc calculate similarity (term X term)
sim21 <- simDoc(docMatrix2, docMatrix1, norm=TRUE, method="cosine") # scores > 2.5 are similar
sims <- simSum(sim21) # closely similars
sims[[1]][1:10]
sims[[2]][1:10]

length(sims[[1]])/len1
length(sims[[2]])/len1 len3 <- length(foley.clust$index[[2]])

doc3 <- data.frame(gu$text[sort(foley.clust$index[[2]])])
ds3 <- DataframeSource(doc3)
ds3.corpus <- VCorpus(ds3)
dtm3 <- DocumentTermMatrix(ds3.corpus, control=list(weighting=function(x)
                weightTfIdf(x, normalize=FALSE), stopwords=TRUE))
docMatrix3 <- t(as.matrix(DocumentTermMatrix(ds3.corpus)))

sim23 <- simDoc(docMatrix2, docMatrix3, norm=TRUE, method="cosine") # scores > 2.5 are similar
sims3 <- simSum(sim23) # closely similars
sims3[[1]][1:10]
sims3[[2]][1:10]

length(sims3[[1]])/len3
length(sims3[[2]])/len3
```

FIG. 9C

BASED ON RECENT NOTES ENTERED BY YOU AND/OR YOUR COLLEAGUES, IT APPEARS THAT THIS PATIENT HAS FEATURES SIMILAR TO ONES IN WHOM A FOLEY CATHETER IS INDICATED. DOES THIS PATIENT HAVE ACUTE URINARY RETENTION?

⊘ YES  ⊗ NO

DO YOU EXPECT THE PATIENT'S URINARY OUTPUT AND ABILITY TO URINATE (IN THE LAVATORY OR A BEDPAN) LIKELY TO IMPROVE IN THE NEXT 6 TO 8 HOURS SUCH THAT CATHETERIZATION WOULD THEN NOT BE INDICATED?

⊘ YES  ⊗ NO

DOES THE PATIENT HAVE ANY STAGE III OR IV PRESSURE ULCERS IN THE LOWER BACK, TRUNK, BUTTOCKS, OR HIP AREAS?

⊘ YES  ⊗ NO

DOES THE PATIENT HAVE A SEVERE MOBILITY IMPAIRMENT, WHICH MAKES POSITIONING OR CLOTHING CHANGES UNCOMFORTABLE FOR THE PATIENT?

⊘ YES  ⊗ NO

DOES THE PATIENT HAVE NEUROGENIC BLADDER?

⊘ YES  ⊗ NO

*FIG. 10.*

DETERMINING PATIENT CONDITION FROM UNSTRUCTURED TEXT DATA

CROSS-REFERENCE TO RELATED APPLICATIONS

This application claims the benefit of U.S. Provisional Application No. 62/087,514, titled "Determining Patient Condition From Unstructured Text Data," filed Dec. 4, 2014, this application also claims the benefit of U.S. Non-Provisional application Ser. No. 14/960,249, titled "Determining Patient Condition From Unstructured Text Data" filed Dec. 4, 2015, which are hereby expressly incorporated by reference in their entirety.

BACKGROUND

Attempts to produce artificial intelligence-based diagnostic decision support systems for the task of diagnosis have failed for many reasons. In some cases, the presentation of patients is so widely-varied that it is difficult for an artificial intelligence system to adequately represent the diversity of the phenomena that characterize each condition. For these, the sensitivity and specificity are low, as are the positive predictive value (PPV) and negative predictive value (NPV). In other cases, the non-sequential evolution of a clinical condition, with periods of exacerbation and remission, leads to an intermittency of features such that various predicates associated with the condition are frequently absent, such that the resulting predictive model or system experiences an excessive rate of false-negative determinations in persons who do indeed have the condition.

In other cases, the severity or frequency of the condition exhibits a wide range, and a system that is capable of detecting severe or frequent disease is not adequately capable of recognizing less-severe instances of the same disease. In yet other cases, the number of features needed to produce a system with adequate statistical sensitivity and specificity is so large that it is not practical (for reasons of time, expense, or other factors) to expect any clinician or set of clinicians to supply non-null values for all of, or a sufficient number of, the features required in a fashion that adds to their workload or intrudes upon and disrupts their customary workflow patterns. In still other cases, the style and mode of the system's interaction with the clinician users interferes with the credentials-based, fiduciary role that the clinician has with regard to the patient's care; the system may have less information upon which to base its conclusions or advice, yet it nonetheless acts in a way that may contradict determinations that the clinician has already reached, appearing to countermand the authority and responsibility that lodges with the clinician and, perhaps, augmenting the clinician's risk of medical malpractice claims or other exposures.

In other cases, the decision support system's operations were slow or logistically discordant with the conduct of the care services process, such that the advice provided by the system was tardy, delivered too late to be of use for prevention or therapeutic decisions. Ex post corroboration of decisions that have already been made is of very low value, but ex post discorroboration of decisions that cannot be amended, undone, or redone is of negative value and vehemently disliked.

In yet other cases, the decision support system is only suited to one-time application, assisting in resolving a diagnosis at the time of presentation, and is not amenable to repeated, ongoing application in the care of a patient over time, as certain conditions that were active become suspended or inactive or cured while other new conditions supervene and become active or previously-suspended ones become reactivated.

Despite long and intense effort, to date no broadly effective approach to automatically recommend nosologic entities or conditions based on the content of unstructured clinical narrative has yet appeared.

SUMMARY

Systems, methods and computer-readable media are provided for optimizing the process of recognizing and ascribing clinical conditions or diagnoses to patients. Some embodiments further include: suggesting these conditions or diagnoses to the attending clinicians; notifying other appropriate health services personnel, such as by emitting a list or notice to those personnel who are users of an online computer-based system, such as an electronic health record (EHR) system; modifying, updating, or generating an electronic health record, in an EHR data base, associated with the patient to include information about the ascribed condition(s) or diagnosis, and/or selecting or modifying a health care treatment plan, which may be embodied as a computer program or routine, for confirming the condition or diagnoses such as by scheduling lab orders, consults, or other patient evaluation, or for facilitating management of the treatment further diagnoses of the condition(s) or diagnosis. Some embodiments utilize structured topic models to allow for latent topics or concepts to be automatically inferred from text, such as unstructured clinical narrative data.

In particular, embodiment of the invention facilitate collecting and analyzing unstructured text data from the electronic health record that accrues during the routine provisioning of care services; to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient. In this way, embodiments of the invention enable reliable determination of relevant differential diagnosis and potential problem list items contemporaneously with the provisioning of care services and in a manner that relies on text that is spontaneously generated as a by-product of the documentation of routine care, which does not require changes to clinician workflow or labor-intensive and cognitively-demanding "Tell-and-Ask" interactive dialogue with users. Accordingly, such embodiments provide a significant improvement in health care technology for patient diagnoses by enabling such determinations of relevant differential diagnosis or potential problem list items to be provided contemporaneously.

According to one aspect, an embodiment of the invention is provided which includes a system for dynamically directing the care process for single and multi-conditions at key points in time to provide decision support using contextually intelligent aware components. For example, relevant labs, findings, medications, and procedures can be presented to a user flexed or tailored to the user, such as a user-specialty, role, venue, clinical condition(s), or other attributes. Some embodiments further include one or more software agents or software routines implemented across a distributed cloud-computing platform for facilitating the services. In some embodiments, the agents or routines are autonomous or semi-autonomous, adaptive, and capable of machine-learning. In so doing, embodiments can provide predictive, preventative, screening and monitoring services, in addition to diagnostic and therapeutic services, for patient conditions and events including overlapping concurrent, multi-condition and multi-diagnoses.

Accordingly, in one aspect, a method is provided for assessing a human patient to determine the likely presence or absence of one or more patient conditions or to suggest which conditions are comparatively more likely than others and merit consideration by the clinicians who are attending the patient. The one or more patient conditions may be determined using structural topic modeling (STM) to statistically assess the patent based on a plurality of unstructured textual records pertaining to observational findings, subjective complaints, clinical assessments, and progress and diagnostic and/or therapeutic plans regarding the patient's care. In particular, STM may be used to establish possible cluster membership of the present patient in one or more reference clusters associated with various known conditions prevailing in or absent from a corpus of textual records resulting from the care processes conducted in a set of prior historical patients and such as have been determined from the corpus. In some embodiments, cluster membership for the patient may be established by calculating a quantitative lexical distance between documents associated with the patient and documents of exemplar members of condition-associated clusters determined by STM modeling of an historical-patient corpus. Further, in some embodiments, identification of the terms or word-stems that are most strongly associated with particular concepts or topics denoting clinical conditions or diagnoses is performed using an Expectation-Maximization algorithm. Still further, in some embodiments a determination of the lexical distance of the current texts to exemplars in labeled clusters of historical texts is performed by calculating the vector cosine of elements denoting the presence or absence in the current texts, of term stems extant in the historical cluster members.

Examples of decision support services provided by some embodiments of the disclosure, and which may be carried out using one or more computer programs, routines, or health care software agents, include providing timely contextual information about patients including condition risks, risk factors and relevant clinical information components that are dynamically updatable; imputing missing patient information including information needed to provide diagnoses, recommendations, or decision support; dynamically generating assessments for obtaining additional patient information based on context, such as caregiver specialty; data-mining and information discovery services including discovering new knowledge, such as new clinical variables associated with clinical conditions or events; identifying or evaluating treatments or sequences of patient care actions and behaviors, and providing recommendations based on this information; intelligent, adaptive decision support services including identifying critical junctures in patient care processes, such as points in time that warrant close attention by caregivers; near-real time querying across diverse health records data sources, which may use diverse clinical nomenclatures and ontologies; improved natural language processing services; and other decision support services.
modifying, updating, or generating an electronic health record, in an EHR data base, associated with the patient to include information about the ascribed condition(s) or diagnosis, and/or selecting or modifying a health care treatment plan, which may be embodied as a computer program or routine, for confirming the condition or diagnoses such as by scheduling lab orders, consults, or other patient evaluation, or for facilitating management of the treatment further diagnoses of the condition(s) or diagnosis.

BRIEF DESCRIPTION OF THE DRAWINGS

The present invention is described in detail below with reference to the attached drawing figures, wherein:

FIG. 3A depicts example clinical narratives (unstructured text information) used as training data for determining reference condition clusters;

FIG. 3B depicts example word stems associated with ten topics discovered from the nursing progress note narratives, shown in FIG. 3A, corresponding to patients with and without Foley catheters in accordance with an embodiment of the invention;

Figures 4C, 4D:
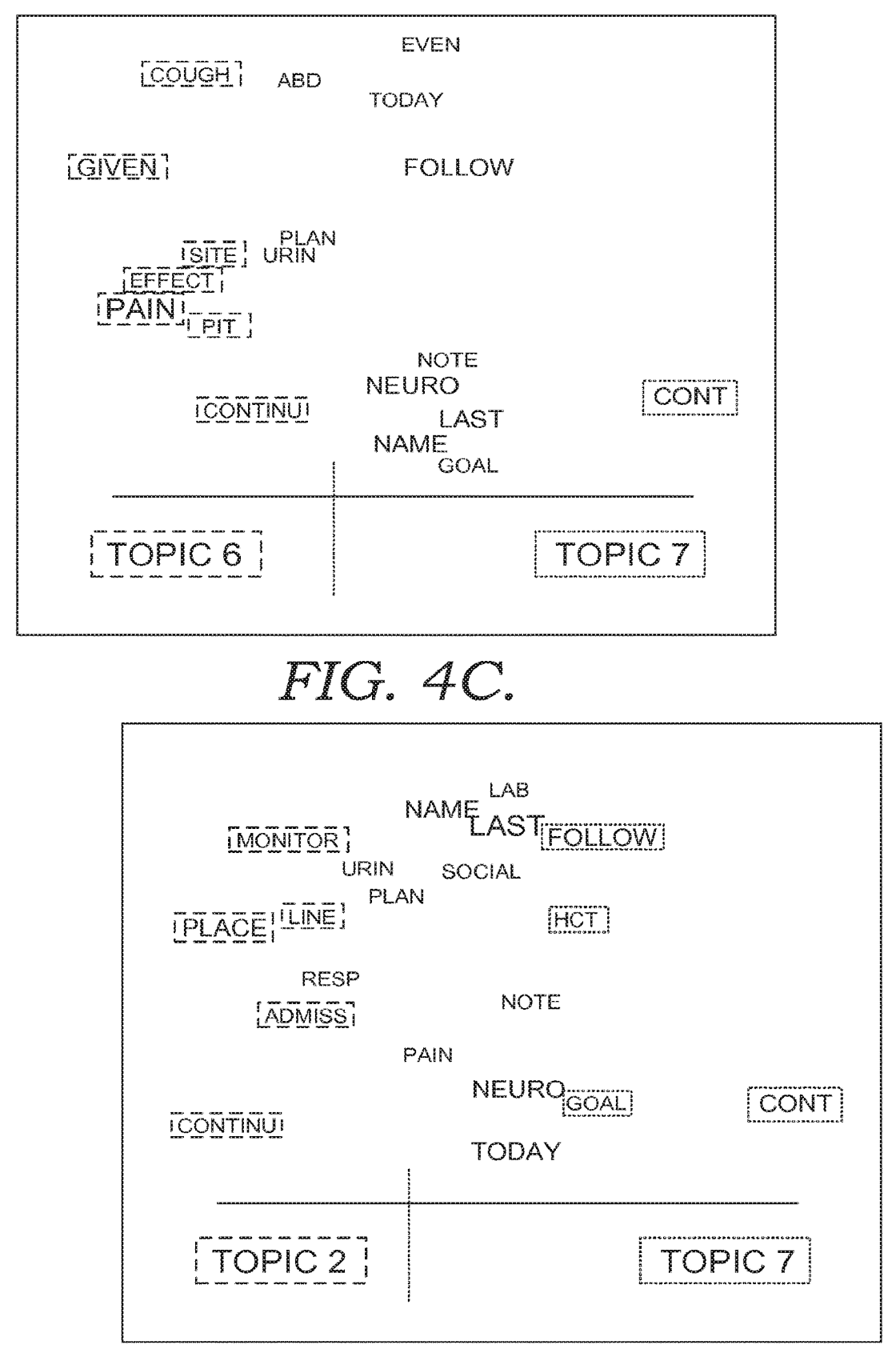

FIGS. 4A-4F depict word-cloud perspective diagrams for topics discovered in unstructured nursing progress note narrative for in-patients with and without Foley catheters;

FIG. 7B shows the classification accuracy of an embodiment of the invention for the Foley catheter example;

FIGS. 9A-9C illustratively provide an example embodiment of a computer program routine used for generating reference condition clusters from a historical text corpus of clinical narratives and determining and likely clinical condition (via cluster membership(s)) for a particular patient, which may be used in the methods described in FIGS. 2A and 2B; and FIG. 10 depicts a series of questions presented to a care giver based on the results of an embodiment of the invention reduced to practice, in order to confirm or (further increase the likelihood) that a patient has a condition (here, clinically indicated Foley catheter insertion.

DETAILED DESCRIPTION

Figure 1A:
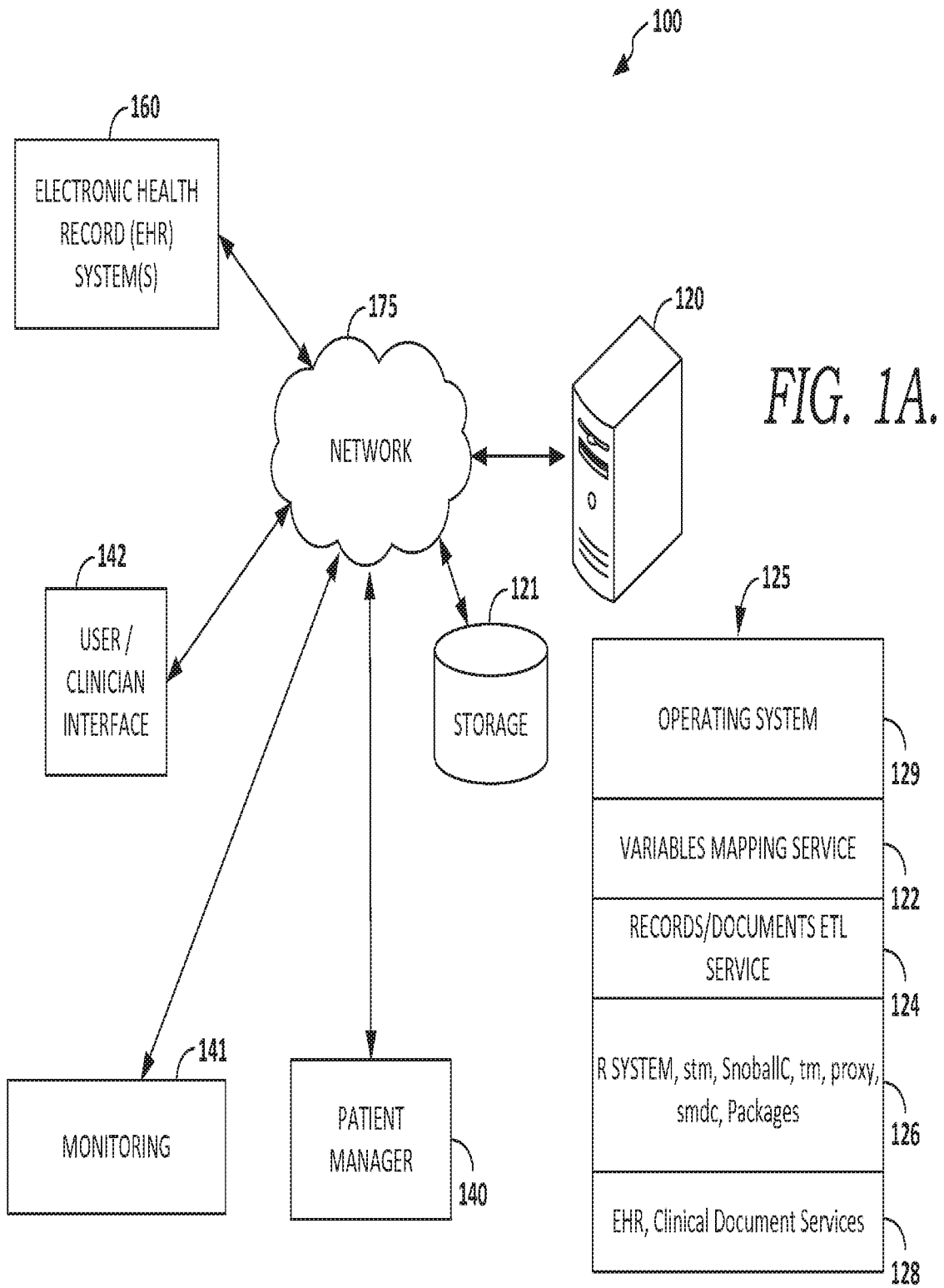
FIGS. 1A and 1B depict aspects of an illustrative operating environment suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for facilitating clinical decision support and managing patient population health by health-related entities including caregivers, health care administrators, insurance providers, patients, and other entities. Triggered by deposition of clinical text documents, an embodiment of the invention includes a structural topic model (STM) system for determining latent concepts that are manifested in unstructured narrative text documents, such as nursing progress notes, that are produced during the course of a patient's care. Discovering such latent concepts in ad hoc narrative text—concepts such as have not previously been formally asserted in the findings or problem list or patient's nominal list of active diagnoses, but are nonetheless likely to prevail at the time of the text's authoring—enables dynamically directing the patient's care processes; coupling with contextualized decision support information for determining next actions, using information from care plans and pathways, in some cases; discovering and incorporating, into decision support services, new ontologies, and behavior generation, sensory perception, and world modeling to achieve adaptive goals.

Some embodiments of the invention are provided for optimizing the process of recognizing and ascribing clinical conditions or diagnoses to patients and in some embodiments, suggesting these conditions or diagnoses to the attending clinicians and/or notifying other appropriate health services personnel, such as by emitting a list or notice to those personnel who are users of an online computer-based system, such as an electronic health record (EHR) system. Some embodiments utilize statistical topic models to allow for latent topics or concepts to be automatically inferred from text, such as unstructured clinical narrative data. Such topic models are referred to as "unsupervised" methods because they infer rather than assume the content of the topics under study, and they have been used across a variety of fields. This is conceptually different from "supervised" methods where the analyst defines the topics ex ante, usually by hand-coding a set of documents into pre-established categories. In particular, embodiment of the invention facilitate collecting and analyzing unstructured text data from the electronic health record that accrues during the routine provisioning of care services; to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

As described previously, the task of diagnosis (analyzing available data to determine a cause that explains the patient's signs and symptoms) is often difficult. The diagnostic process (deciding which questions to ask and answer; which tests to perform; which alternative differential-diagnostic considerations to entertain; deciding the relative value of the results from the foregoing, compared to the associated risks and financial costs of pursuing answers to various questions) is itself equally challenging.

However, the implementation of electronic health records (EHRs) presents a new opportunity to enhance computer-assisted diagnosis in routine practice. EHRs contain many of the data elements critical to establishing a differential diagnosis. Most EHRs' databases contain a patient problem list. The problem list is described as a key opportunity as a storage modality and workflow moment to offer clinicians diagnostic support. In point of fact, however, a majority of clinicians tends to staunchly refrain from ascribing problem list items in EHRs in a manner that is contemporaneous with their conduct of the care process. Some opine that concurrent attribution of problem list entries is not convenient in their workflow; others assert that they do not wish to create a documentation trail of contemporaneously-entered problem list items that might be utilized by attorney-for-plaintiff in subsequent malpractice claims.

Furthermore, autopsy studies and other research suggest an overall diagnostic error rate of at least 30% in medicine. Most of these are errors-of-omission and failures-to-diagnose (including "failure to diagnose in a timely fashion"), due to cognitive mistakes on the part of the individual practitioner. Premature closure, overconfidence, anchoring and a host of other cognitive mistakes play a role in diagnostic error. While older efforts in diagnostic support have required entry of patient symptoms and signs and other patient features, more recent approaches, including systems that automatically retrieve EHR and other contemporary data that allow to begin with either a problem, a presumed diagnosis, a drug, a symptom, or a constellation of any of the above, still fail on account of the errors-of-omission and failures-to-diagnose on the part of the human clinicians. The clinician user is frequently unable to adequately interact with the diagnostic decision support systems that depend on human review and input.

In that regard, decision support systems such as Cerner Corporation's DiscernExpert™ system play a more active and operational role, providing decision-support as a by-product of transaction-processing and inferencing. Such systems do not passively wait for physicians or other health workers specifically to request assistance but instead actively transact provisional orders or emit "alert" messages or interdict transactions that are unsafe or otherwise contraindicated or perform other actions autonomously. Nevertheless, diagnostic decision support is not a prominent aspect of how such systems are utilized, despite the fact that those systems are functionally capable of assisting with diagnoses. The reasons why this is so are substantially the same as the limitations described above in the preceding paragraphs.

Moreover, faulty designs for human-computer interaction and inadequate recognition of the logistical and psychological aspects of clinical decision support system use account for a major portion of the failures represented in other approaches, and despite various partial successes, these other approaches continues to have several limitations including: (1) Excessive false-negative rates, often exceeding 40%.

(2) Excessive consumption of time for entry and/or review of findings, before the system calculates its classifications or advice.

(3) Failure to accommodate different stages in the conditions' evolution, or different levels of severity of manifestation of conditions' characteristic features, or intermittency of the presence or observability of certain features.

(4) Failure to identify conditions other than 'medical' diagnoses.

(5) Proneness to misclassification and calibration errors arising from model development in a population of patients that is different from the population that is incident upon the institution where the current patient is receiving care, or development in a health services facility where various factors affecting clinicians' generation of clinical narrative text (factors including staffing levels; workload; the regime of prevalent linguistic expressions in clinical text; the regulations and tort or other normative factors that affect the structure and content of clinical narrative in the jurisdiction; the modes of documenting symptoms and objective findings and clinical assessments and plans; and so forth) are substantially different from those where model development occurred.

(6) Requirement to utilize numerous signs and symptoms that require considerable time to enter, to retrieve, or to review and affirm even when they are presented to the user automatically by an online system.

(7) Process and workflow intrusions that interfere with ongoing work for the clinician, such that they are disincentivized to permit the intrusions or unrequested demands for her/his time and attention.

(8) Failure to incorporate the observations and assessments of multiple clinicians, including clinicians different from the current user, such as most commonly are recorded in unstructured narrative text segments of the EHR.

(9) Inability to include longitudinal time-series evidence for conditions whose time-trajectory constitutes a significant form of evidence characterizing the conditions, including expressions that are recorded in serial unstructured progress note texts that are date-time stamped at the moment of their deposition in the EHR.

(10) Requirement that the user know many or all of the patient's diagnoses or clinical context and be able at the outset to nominate or select these, or to identify sequences in regard to which diagnoses or conditions arose in which order. However, many patients have multiple concurrent/comorbid diagnoses, such that knowing and remembering all of them in a fashion that could be accurately and completely recited into a decision support system is error-prone or cumbersome. Yet other patients have not yet received a diagnosis or diagnoses established at other health institutions are not available or known to the user, such that reciting information that is elsewhere known is (a) not possible for a given individual clinician user at the time that diagnostic decision-making proceeds in the current episode or (b) error-prone insofar as sequences of conditions or diagnoses are not known with adequate certainty.

(11) Lack of automatic adaptation to the longitudinally evolving context or physiologic condition of the patient, vis a vis changing and adjusting selections under (10) with the passage of time.

Accordingly, it is therefore highly valuable and highly desirable to provide embodiments of the methods and systems described herein for ameliorating these limitations and providing objective, quantitative means for automatically discriminating true-positive versus false-positive conditions in near-realtime, to enable diagnostic and therapeutic decision-making to proceed without delay.

Referring now to the drawings in general, and initially to FIG. 1A in particular, an aspect of an operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of the invention including collecting and analyzing unstructured text data from electronic health record(s) to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example.

Although FIG. 1A depicts an exemplary EHR system 160, it is contemplated that an embodiment relies on user manager or patient manager 140 and/or monitor 141 for storing and retrieving patient record information such as information acquired from monitor 141.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future events such as acute risk of deterioration are determined according to the embodiments presented herein. Embodiments of interface 142 also facilitates accessing and receiving information from a user or health care provider about a specific patient or population of patients including patient history; health care resource data; variables measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, manager 140 includes a Web-based application or set of applications usable to manage user services provided by an embodiment of the invention. For example, in an embodiment, manager 140 facilitates processing, interpreting, accessing, storing, retrieving, and communicating information acquired from monitor 141, EHR 160, or storage 121, including candidate diagnoses or conditions determined by embodiments of the invention as described herein. In an embodiment, manager 140 sends a notification (such as an alarm or other indication) directly to user/clinician interface 142 through network 175. In an embodiment, manager 140 sends a maintenance indication to provider clinician interface 142. In one embodiment of manager 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, manager 140 is communicatively coupled to monitor 141 and to network 175. In an embodiment, patient monitor 141 communicates via network 175 to computer 120 and/or provider clinician interface 142.

In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, and which may be acquired periodically or as one or more time series. In an embodiment, monitor 141 comprises patient bedside monitor, such used in hospital. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patients' blood pressure and enters the measurement and/or observations via manager 140 or interface 142. In another example, a nurse or caregiver enters one or more progress notes for an in-patient via manager 140 or interface 142. A portion of such progress notes are illustratively shown in FIG. 3A, which depicts a set of nursing progress note narratives for in-patients with and without Foley catheters and which is used an training data for an embodiment of the invention that was reduced to practice.

Examples of physiological variables monitored by monitor 141 can include, by way of example and not limitation, heart rate, blood pressure, oxygen saturation (SoO2), central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making. For example, in some embodiments, monitor 141 may be used for acquiring, determining, or characterizing (by a human caregiver) other types physiological variables such as, muscle activity which might be sensed from electromyogram signals, eye movement which might be sensed from electro-oculogram signals, or other biometric information. In an embodiment, a monitor such as 141 comprises a sensor probe, such as an EEG probe, and a communication link that periodically transmits identification information and probe data to patient manager 140, so that the time series of monitored values is stored on patient manager 140, enabling the patient manager to form a raw binary alarm indication and/or a physiological variable decision statistic. In an embodiment, patient monitor 140 collects raw sensor information, such as optical sensor 184, and performs signal processing, such as movement detection, kinematic modeling, distance and shape processing, velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, manager 140, interface 142, and/or computer system 120.

An embodiment of monitor 141 stores user-derived data locally or communicates data over network 175 to be stored remotely. In an embodiment, manager 140 is wirelessly communicatively coupled to monitor 141. Manager 140 may also be embodied as a software application or app operating on a user's mobile device. In an embodiment, manager 140 and monitor 141 are functional components of the same device, such as a device comprising a sensor and a user interface. In another embodiment, manager 140 is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping (or indexing) service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke software services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, stm (statistical topic modeling), SnoballC, tm, proxy, and smdc packages, or similar services. In an embodiment, computation services 126 include the services or routines, which may be embodied as one or more software agents or routines such as the example embodiments of computer program routines illustratively provided in FIGS. 9A-9C. In some embodiments, software services 126 use EHR or clinical document services 128, which provide a framework for accessing and processing text corpuses such as unstructured clinical narratives of patient information. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
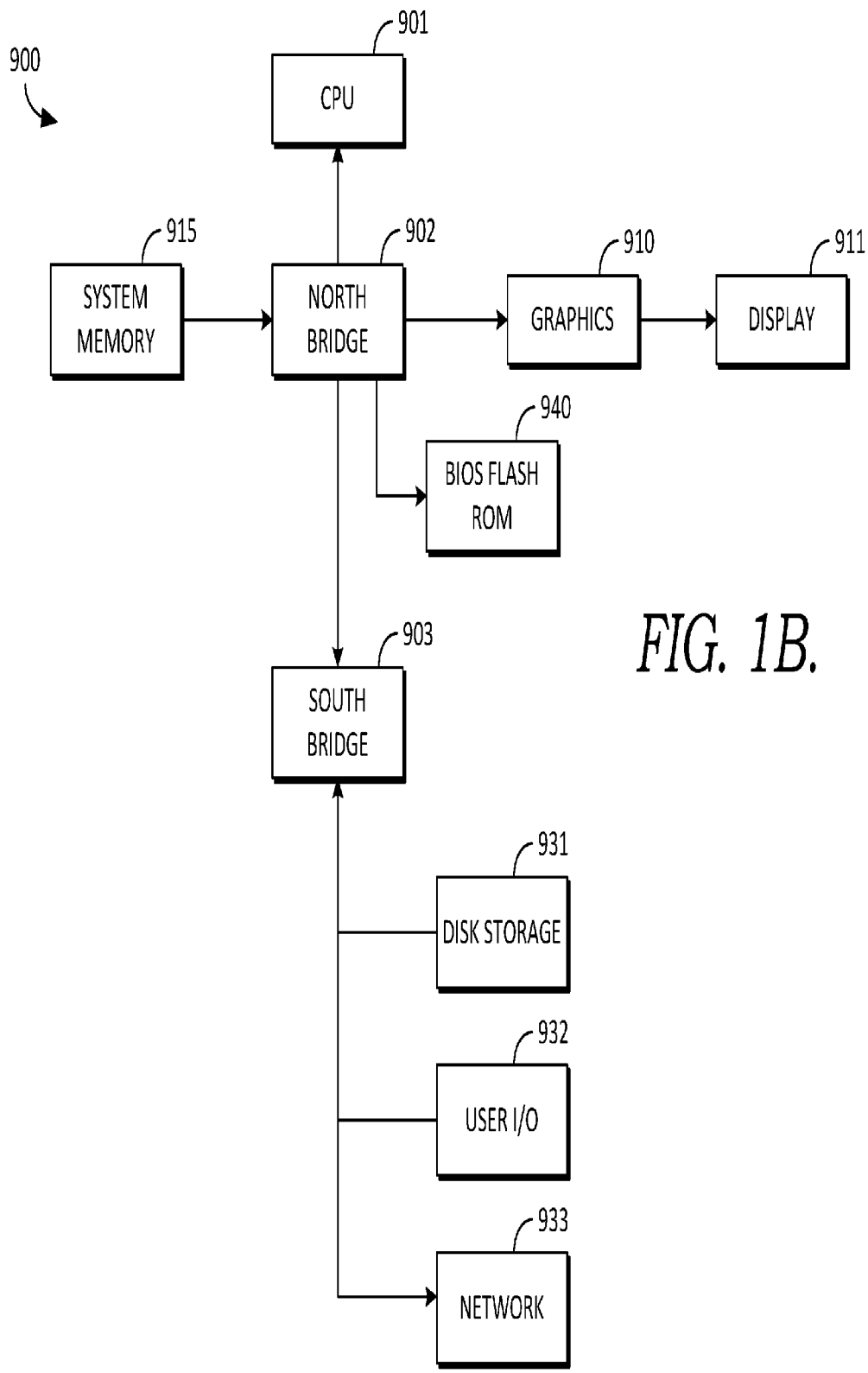

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2A:
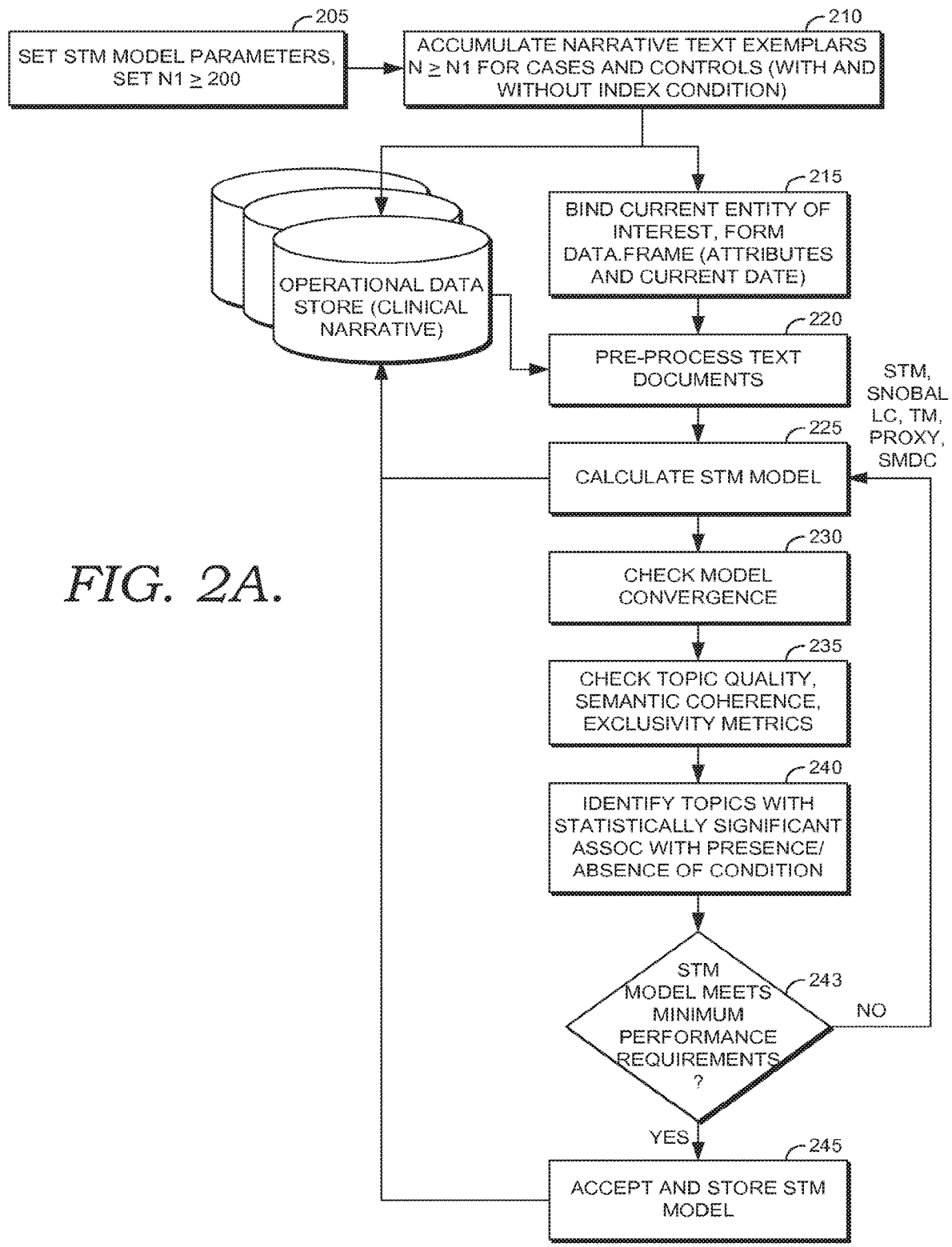
FIG. 2A depicts a flow diagram of a method for generating reference condition clusters from a historical text corpus of clinical narratives, in accordance with an embodiment of the invention.
Figure 2B:
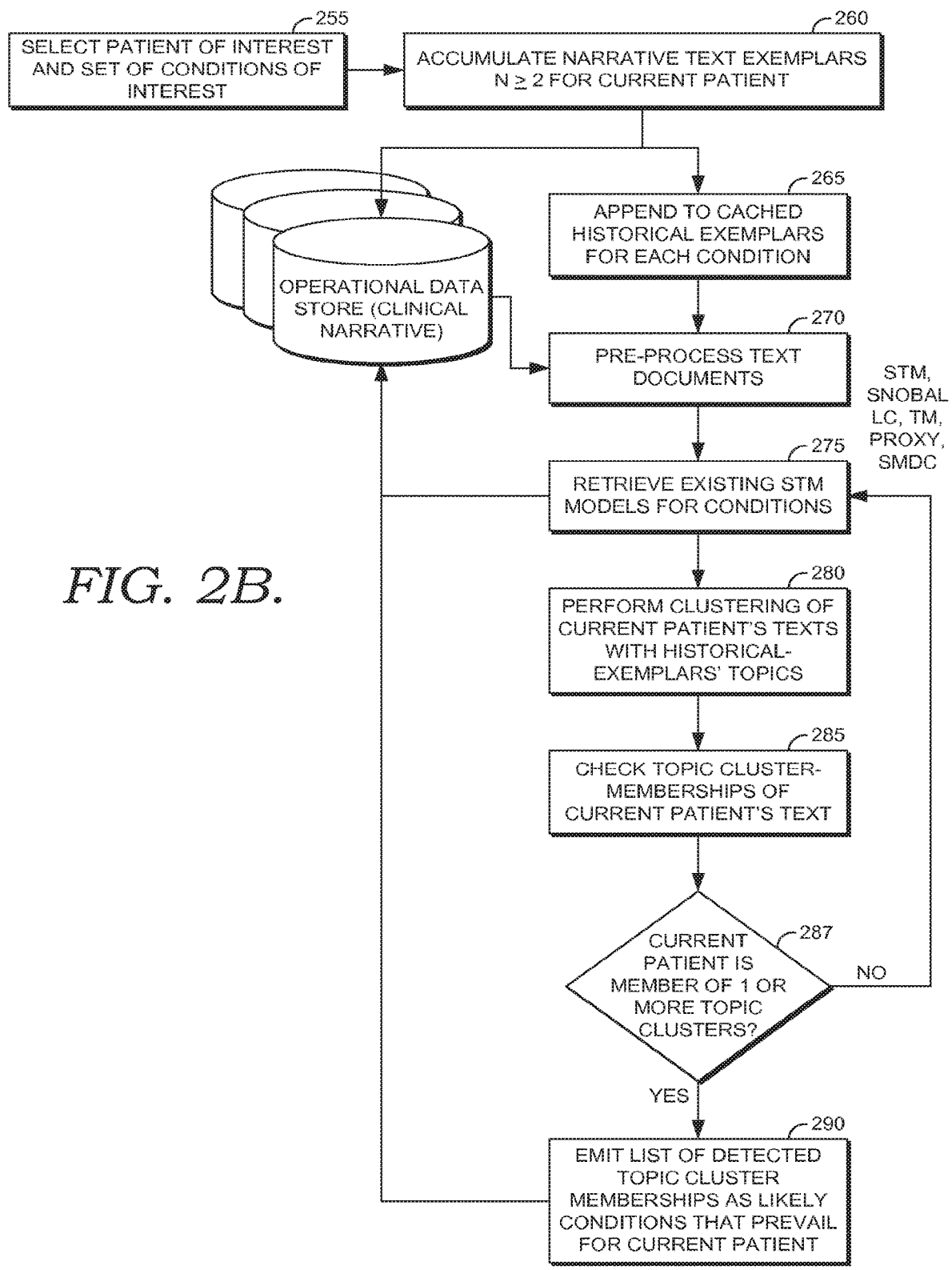
FIG. 2B depicts a flow diagram of a method for determining and likely clinical condition (via cluster membership (s)) for a particular patient based on unstructured clinical narratives associated with the patient in accordance with an embodiment of the invention.
Figure 4A:
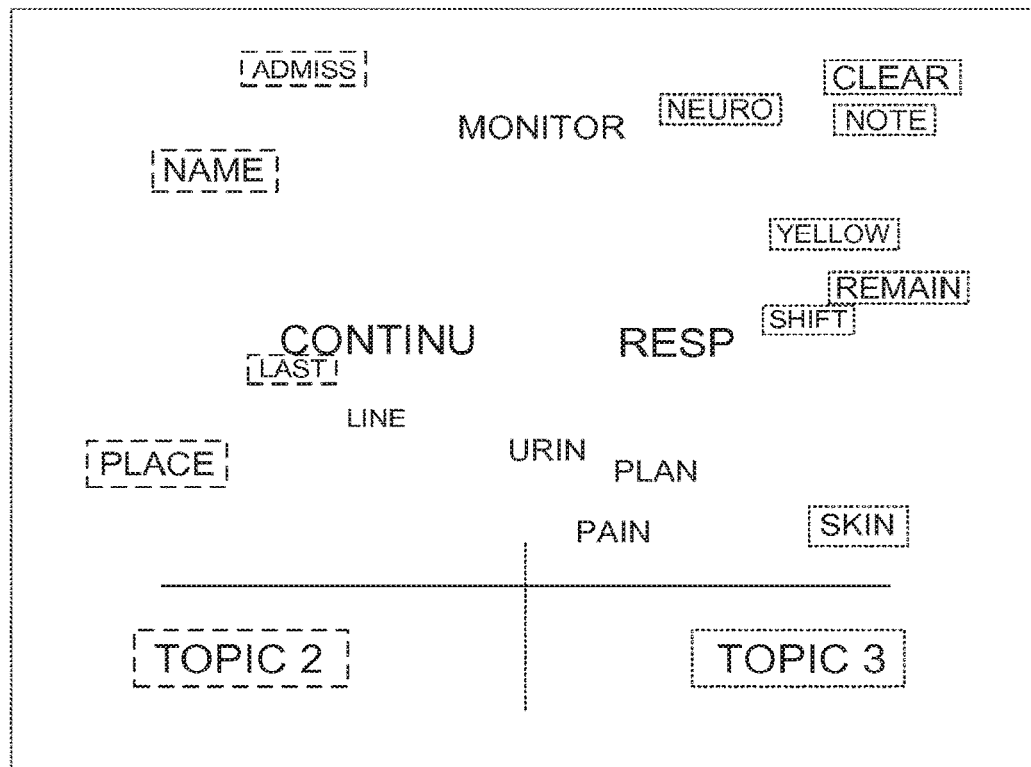
Figure 4B:
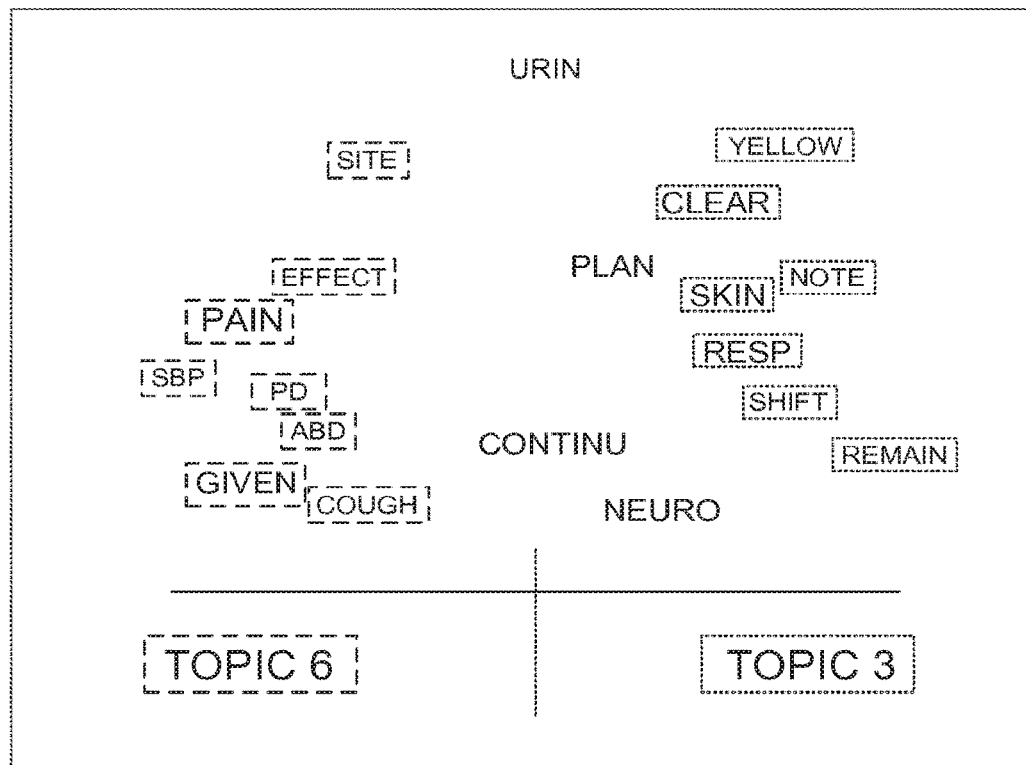
Figure 4E:
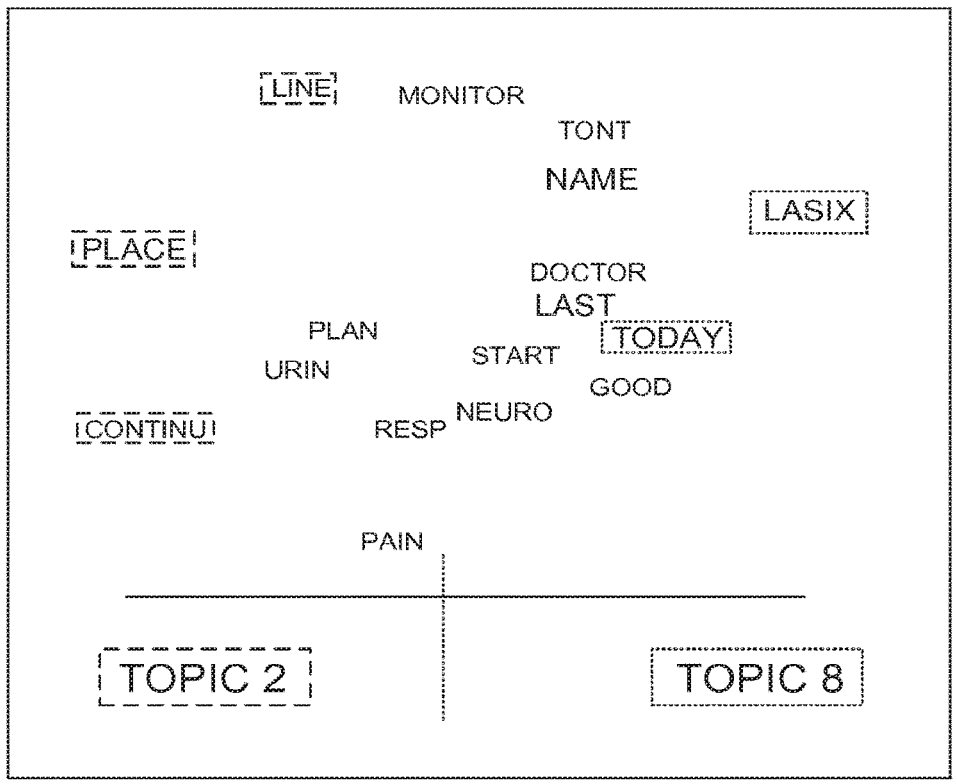
Figure 4F:
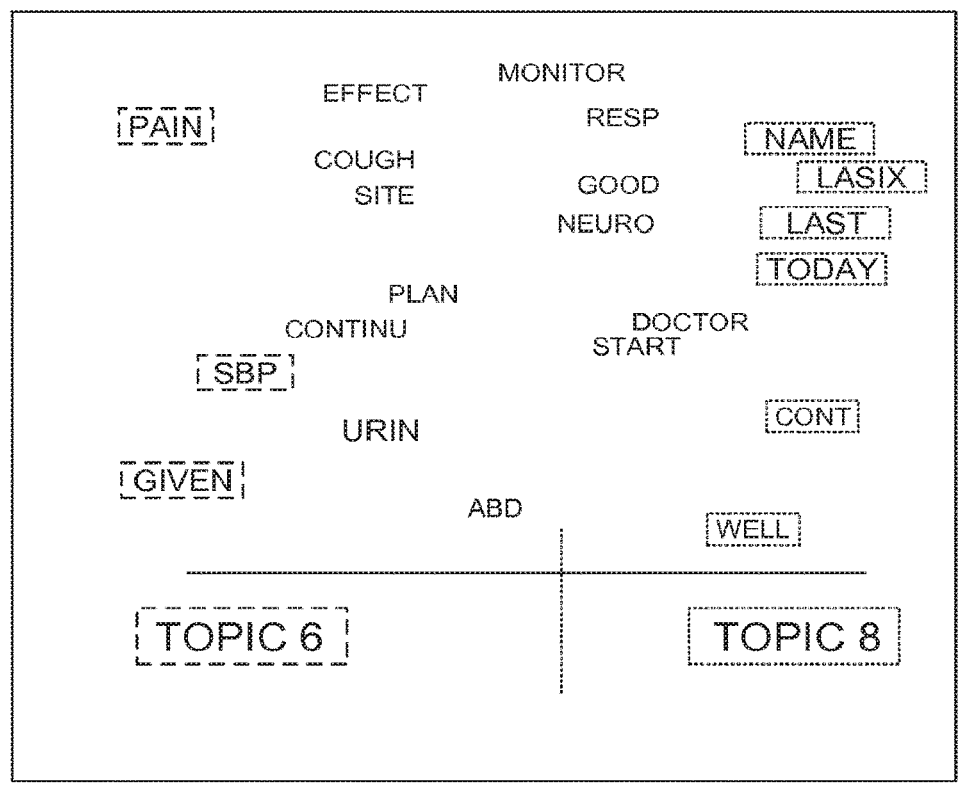

Turning now to FIGS. 2A-2B, example embodiments of a first method 200 for generating reference condition clusters from a historical text corpus of clinical narratives, and an example embodiment of a second method 250 for determining and likely clinical condition (via cluster membership (s)) for a particular patient based on unstructured clinical narratives associated with the patient, are illustratively provided. With reference to these drawings, at a high level, statistical topic models allow for latent topics or concepts to be automatically inferred from text. Within the class of unsupervised statistical topic models, topics may be defined as distributions over a vocabulary of words that represent semantically interpretable concepts or "themes." Topic models may come in two varieties: single-membership models and mixed-membership models. Efforts undertaken in natural language processing focus on single-membership models which have emphasized document meta-data. In mixed-membership models, such as Latent Dirichlet Allocation, a document is represented as a mixture of topics, with each word within a given document belonging to a topic; thus, each document can be represented as a vector of proportions that denote what fraction of the words belong to each topic. In single-membership models, each document may be restricted to only one topic, so all words within it are generated from the same distribution.

Some embodiments of the invention focus on mixed-membership models. In mixed-membership models, each document (indexed by d) may be assumed to be generated as follows. First, a distribution over topics is drawn from a global prior distribution. Then, for each word in the document (indexed by n), we draw a topic for that word from a multinomial distribution based on its distribution over topics ($z_{d,n} \sim \text{Mult}(\theta_d)$) Conditional on the topic selected, the observed word $w_{d,n}$ is drawn from a distribution over the vocabulary $w_{d,n} \sim \text{Mult}(\beta)$ where $\beta_{k,v}$ is the probability of drawing the v-th word in the vocabulary for topic k. Each of these topics is a distribution over words with high-frequency words associated with that topic. LDA assumes a Dirichlet-distributed prior distribution for the topic proportions such that $\theta_d \sim \text{Dirichlet}(\alpha)$. The resulting posterior distributions have many local modes, meaning that different initializations can produce different solutions. This can arise even in simple mixture models with low dimensionality.

STM is different from LDA and other models just described by allowing for the inclusion of meta-data or label covariates of interest into the prior distributions for document-topic proportions and topic-word distributions. The result is a model where each open-ended response is a mixture of topics. Rather than assume that topical prevalence (i.e., the frequency with which a topic is discussed) and topical content (that is, words that are used to discuss a topic) are constant across all participants, the analyst can incorporate covariates over which we might expect to see variance. As in LDA, each document arises as a mixture over K topics. In the STM, topic estimation for LDA proceeds by variational expectation-maximization (EM), where the local variables $\theta_d$ and $z_d$ are estimated for each document in the E-step, followed by maximization of global parameters $\alpha$ and $\beta$.

Variational EM uses a factorized approximation to the posterior. Proportions 0 can be correlated, and the prevalence of those topics can be influenced by some set of covariates X through a standard regression model with covariates θ ~LogisticNormal(Xγ,Σ). For each word (w) in the response, a topic (z) is drawn from the response-specific distribution, and conditional on that topic, a word is chosen from a multinomial distribution over words parameterized by β, which is formed by deviations from the baseline word frequencies. This distribution can include a second set of covariates U (allowing, for example, physicians to use the word "micturition" more frequently than nurses while discussing urine output).

Thus, there are critical differences in the STM as compared to the LDA model described above: (1) topics can be correlated; (2) each document has its own prior distribution over topics, defined by covariate X rather than sharing a global mean; and (3) word use within a topic can vary by covariate U. The covariates provide a way of structuring the prior distributions in the topic model, injecting valuable information into the inference procedure.

STM modeling provides fast, transparent, replicable analyses that require few a priori assumptions about the texts under study. Yet it is a computer-assisted method, and the researcher is still a vital part of understanding the texts, as we describe in the examples section. The analyst's interpretive efforts are guided by the model and the texts themselves. Embodiments of unsupervised STM modeling can relieve the analyst of the burden of trying to develop a categorization scheme "from scratch" and perform the often mundane work of associating text documents with those categories.

In standard LDA, the document collection is assumed to be unstructured; that is, each document is assumed to arise from the same data-generating process irrespective of additional information the analyst might possess. By contrast, our framework is designed to incorporate additional information about the document or its author into the estimation process. This allows us to measure systematic changes in topical prevalence and topical content over the conditions in our experiment, as measured by the X covariates for prevalence and the U covariates for content. Thus, for example, we can easily obtain measures of how our treatment condition affects both how often a topic is discussed (prevalence) and the language used to discuss the topic (content). Using a variational approximation to the posterior distribution, we can propagate our uncertainty in the estimation of the topic proportions through our analysis.

The inference on the STM quantities of interest may be understood by reference to the familiar regression framework. For example, consider topical prevalence; if we observed the topics for each survey response, we could generate a regression where the topic is the outcome variable, and the treatment condition or other author controls (e.g., text type, care venue, clinical specialty, role with regard to the patient's care), along with any interactions, are the explanatory variables. This regression would give us insight into whether our treatment condition caused respondents to spend a larger portion of a text discussing a particular topic.

Figure 5:
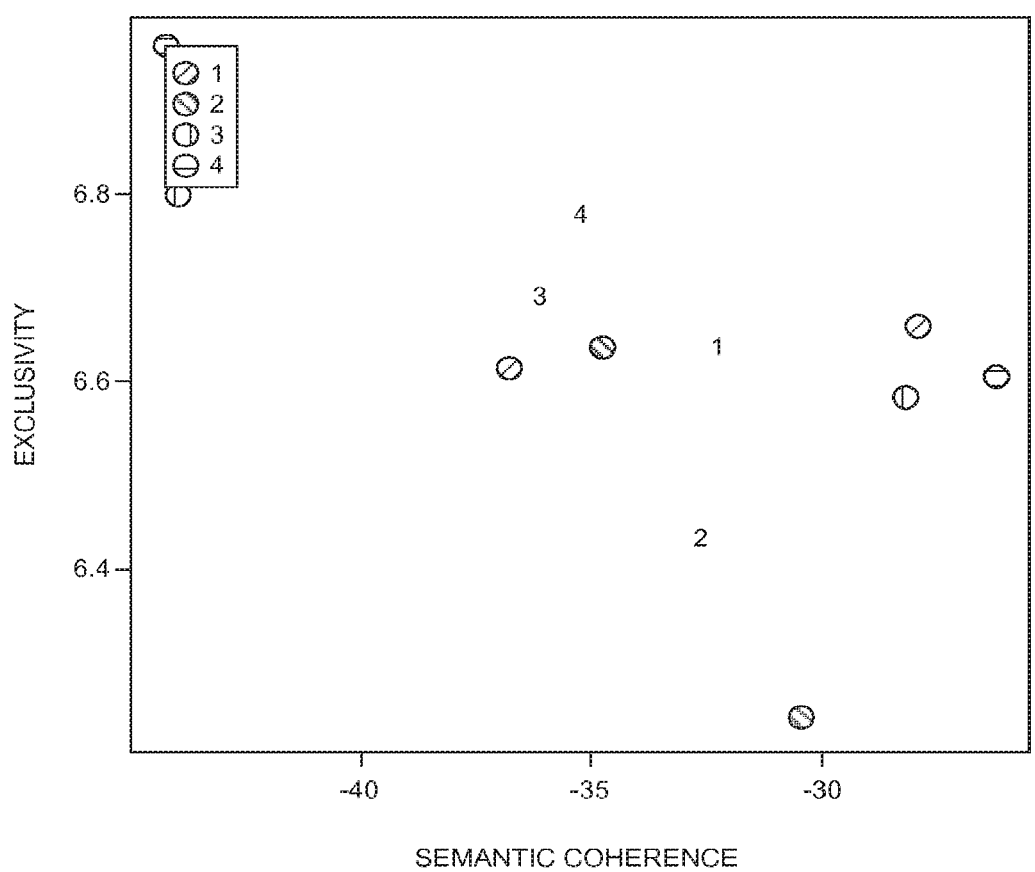
FIG. 5 depicts an example of semantic coherence-exclusivity plot for four top-performing iterations (from among 20 STM runs processing historical/retrospective nursing progress note narrative for in-patients with and without Foley catheters) from among which best model may be selected for use in prediction of conditions prospectively.

Semantic coherence is a quantitative measure based on co-occurrence of top topic words. While semantic coherence is a useful criterion for evaluating linguistic models, it only addresses whether a topic is internally consistent; it does not, for example, penalize topics that are semantically alike. From the standpoint of nosologic inference, in some embodiments we want to ensure that both that we are evaluating a well-defined concept and that our measure captures all incidence of the concept in the clinical texts. For this, we can turn to the exclusivity of topic words. If words with high probability under topic i have low probabilities under other topics, then we say that topic i is exclusive. A topic that is both cohesive and exclusive is more likely to be semantically useful. FIG. 5 shows an example of using semantic coherence-exclusivity for an embodiment reduced to practice and further described in connection to FIGS. 3A and 3B.

Accordingly, in order to select an appropriate model, some embodiments of the invention generate a set of candidate models (generated by differing initializations, tuning parameters, or processing of the texts) and then discard results that have the lowest value for the bound. Some of these embodiments then can automatically select or facilitate a selection a model by plotting the exclusivity and semantic coherence of the remaining models and determining a model that is on the semantic coherence-exclusivity "frontier," that is, where no model strictly dominates another in terms of semantic coherence and exclusivity.

Both LDA and factor analysis support mixed-membership, which allows documents to manifest content of multiple topics simultaneously, but cannot incorporate the rich covariate information that often is present with clinical narrative, whereas the single-membership models can incorporate a narrow set of covariate types and are limited to a single topic per document, which is too restrictive for a diagnostic decision support application. Accordingly, compared to other unsupervised techniques, embodiments of the invention using STM can provide the most versatility in detecting mixtures of latent topics in text documents that arise in the course of addressing multiple clinical needs simultaneously.

With reference to FIG. 2A, one embodiment of a method 200, for developing the structured topic models, comprises the following steps. At step 205, initialize STM parameters, including minimum dataset size (for example and not as limitation: N1≥200) and minimum cluster arity (for example and not as limitation: M≥3). At step 210, acquire a collection of at least N1 samples of historical text documents pertaining to, and arising in the course of, the care of an individual patient for analysis, each document bearing meta-data (labeling) ascribing the presence or absence of one or more conditions that prevailed at the time of the document's authoring for the patient who was the subject of the document. At step 215, bind the record of a target condition predicate or diagnosis entity (from electronic medical records ontology/nomenclature system). At step 220, preprocess the text documents according to means as are known to those practiced in the art of automated natural language processing, including stopword removal, word-stemming, lowercase transformation, and punctuation/whitespace stripping.

At step 225, calculate an STM model associating stemmed terms in the collection of documents with the meta-data labels. Perform multiple Expectation-Maximization (EM) iterations, preferably more than 50 iterations, to determine optimal associations of the stemmed terms with the meta-data labels for the selected number of target clusters M. Some embodiments of step 225 may be carried out using the example computer program routines illustratively provided in FIGS. 9A-9C, which are implemented using the stm, SnoballC, tm, proxy, and smdc R-packages described in connection to FIG. 1A. At step 230, check for convergence of the STM model by examining the iteration-to-iteration objective-function time-series, as a function of iteration index.

At step 235, repeat the EM iterations for separate STM modeling runs, and check these for adequate STM topic-quality metrics, such as maximizing joint semantic coherence and exclusivity. Select the best-performing STM model based on semantic coherence—exclusivity cross-product or an importance-weighted measure of the joint utility of these performance metrics. At step 240, examine the STM model metrics of the selected STM model for each of the induced topics to determine which topics manifest statistically significant association with the target condition or diagnosis predicate.

At step 243, determine that the STM model and the identified topic-clusters meet minimum performance requirements in terms of sensitivity, specificity, F1 measure, overall accuracy, or other measures. If the performance is acceptable, then at step 245 accept and store the STM model and topics and cluster exemplars. If the performance is not acceptable, then return to step 225 to recalculate stm model, using different parameters and/or different text documents.

With reference to FIG. 2B, one embodiment of a method 250, for determining and likely clinical condition(s) (via cluster membership(s)) for a particular patient, comprises the following steps. Embodiments of method 250 are described in the context of applying an existing STM reference model, such as may be determined using method 200, to newly-accruing textual information for an as-yet-unclassified patient. At step 255, determine a target patient of interest and one or more conditions of interest. At step 260, accumulate (or access already accumulated) narrative text exemplars (or unstructured textual data). In some embodiments, retrieve a collection of at least 2 text documents pertaining to, and arising in the course of, the care of an individual patient for analysis, for which meta-data (labeling annotations) ascribing the presence or absence of one or more conditions that prevail at the time of the document's authoring for the patient who is the subject of the documents may or may not have been applied.

At step 265, in some embodiments of method 200 append cached historical exemplars for each condition. Further in some embodiments, bind the records of one or more target condition predicates or diagnosis entities of interest, which may be accessed from electronic medical records ontology/nomenclature system. At step 270, the target patient's text documents are pre-processed using automated natural language processing, such as stopword removal, word-stemming, lowercase transformation, and punctuation/whitespace stripping.

At step 275, retrieve existing STM models for condition (s). In some embodiments, step 275 comprises retrieving or accessing one or more existing STM models and the identified historical topic-document clusters pertaining to the condition predicates or diagnosis concept entities. At step 280, perform clustering of the patient's text data with historical-exemplars topics. In an embodiment, step 280 comprises performing K-means or other clustering of the current patient's pre-processed texts with cluster-member historical exemplar texts.

At step 285, check topic cluster-memberships of the patient's text data. In an embodiment, step 285 comprises calculating a lexical distance of current-patient documents to topic-clusters, to detect which topic-clusters, if any, the current patient's documents are statistically significantly similar to. At step 287, patient membership in one or more topic clusters is evaluated. If the patient is not a member of a topic cluster, then method 250 returns to step 275. If a patient is a member of one or more topic clusters, then method 250 proceeds to step 290.

At step 290, a listing is created or provided of detected topic cluster memberships as likely conditions that prevail for the target patient. In some embodiments, step 290 comprises generating a listing of detected significant cluster-memberships. The listing may be provided to an appropriate human clinician user, typically via electronic health record (EHR) software system, and record evidence of having done so in the EHR. If no cluster-membership condition is ascertained, then the patient is deemed not to presently manifest any of the conditions for which reference clusters have been determined. In such case, no notice is emitted to the human clinician user in an embodiment; however, the system may optionally deposit a date-time-stamped record in the EHR as evidence of the then-negative determination.

With reference to FIGS. 3A-10, an example is provided of one embodiment of the invention reduced to practice for personalized classification as to acute Foley catheter clinical indications. In this example embodiment reduced to practice, a series of nursing progress note data were acquired, from the de-identified records of acutely hospitalized patients with and without indwelling Foley urinary catheters.

FIG. 3A illustratively depicts a portion of this series of nursing progress note data. Records were randomly selected from a patient health records data warehouse, which is derived from Cerner electronic health record (EHR) from 100% of episodes of care that are incident upon the participating health institutions. The personally-identifiable information was removed in conformance with U.S. HIPAA law and regulations, and the de-identified data were stored in a separate, secure database.

This example embodiment was reduced to practice using a computer running the Linux operating system, the open-source statistical software package R and the R module stm, SnowballC, tm, and smdc packages, such as described in connection to FIGS. 1A and 1B. Stream processing of the accruing documents series was accomplished using Ptolemy and Kepler stream-processing software. In this regard, a cloud-based computing configuration is one alternative embodiment of the invention. Alternatively, a stand-alone server or other computing device equipped with suitable connectivity to the device(s) by which the time series are acquired may likewise be utilized in another embodiment.

From data acquired from in-patient hospital subjects and stored in the inventor's organization's datawarehouse, a corpus of nursing progress notes from 200 distinct patients was extracted, 100 each from patients who had a Foley urinary catheter in-place and from patients who did not receive insertion of a Foley catheter during their in-patient episode, as shown in FIG. 3A.

Figure 7A:
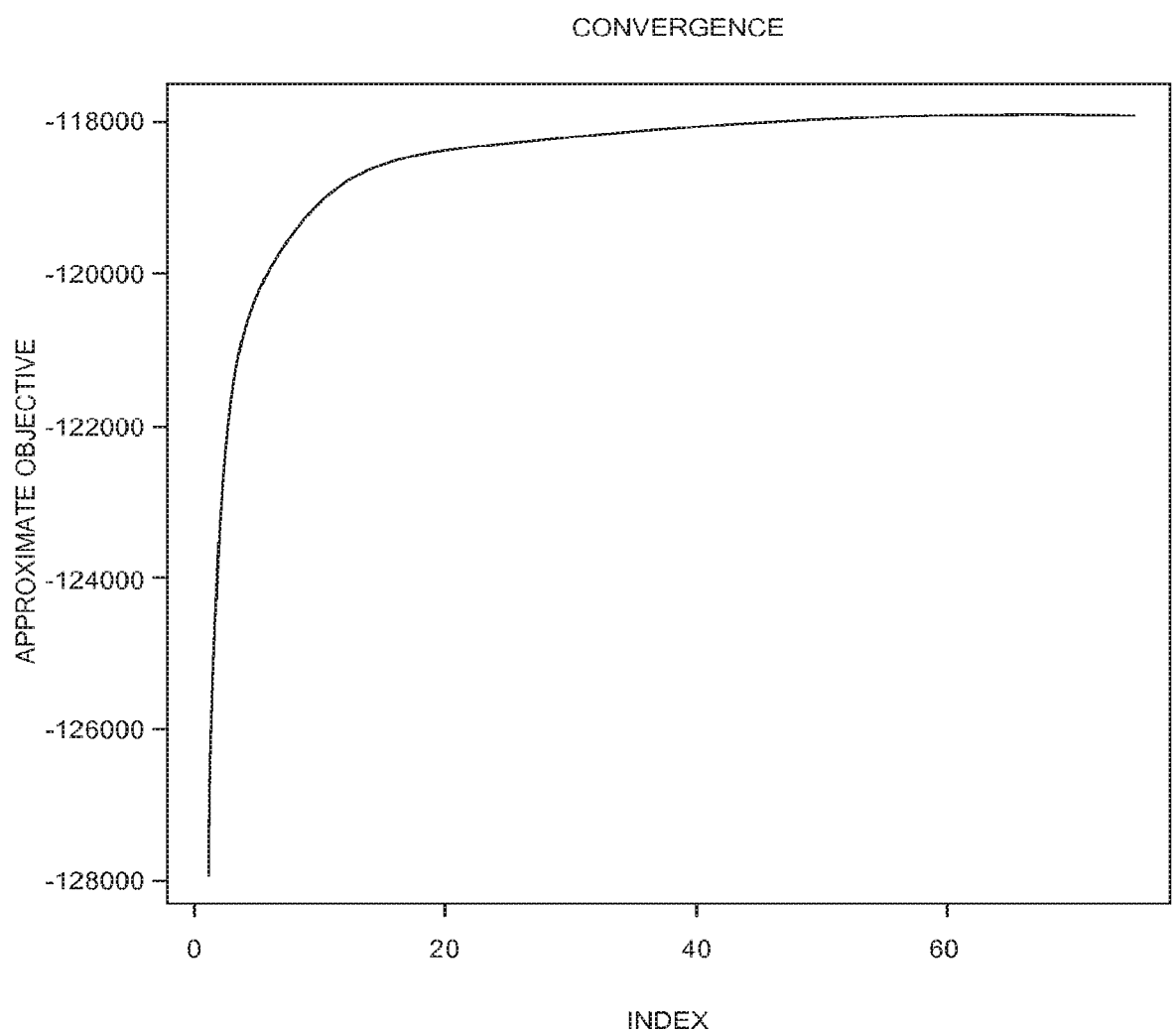
FIG. 7A depicts an example STM Expectation-Maximization convergence for ten topics discovered in nursing progress note narrative for in-patients with and without Foley catheters in accordance with an embodiment of the invention.

Using word-stemming and transformations such as are supported in open-source software packages stm, SnowballC, and tm, implemented in the example computer program routines depicted in FIGS. 9A-9C, an example application of the embodiment reduced to practice using the data from FIG. 3A was able to identify positive cluster-membership with 96% sensitivity and 92% specificity, as shown in FIGS. 7A and 7B.

Figure 6:
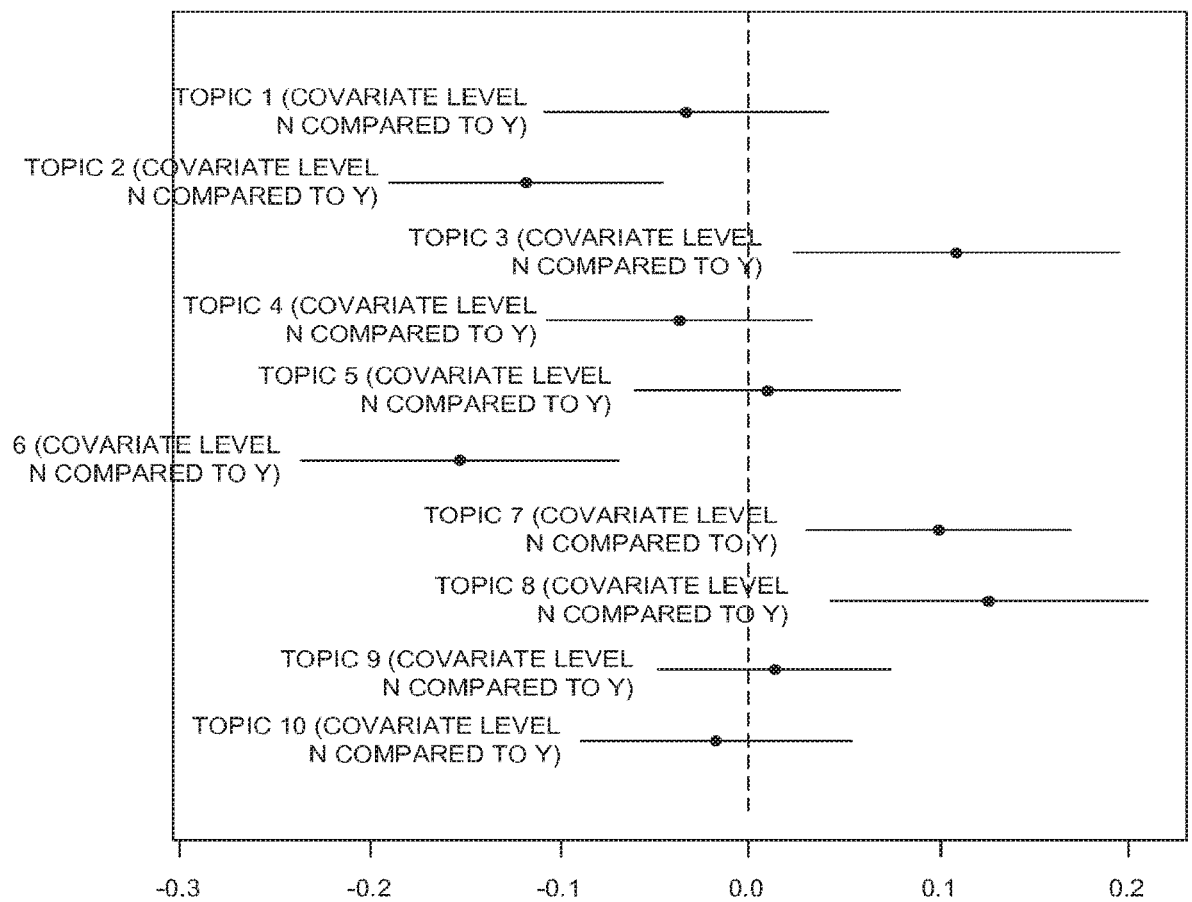
FIG. 6 depicts an example effect-size plot for ten topics discovered in nursing progress note narrative for in-patients with and without Foley catheters.
Figure 8:
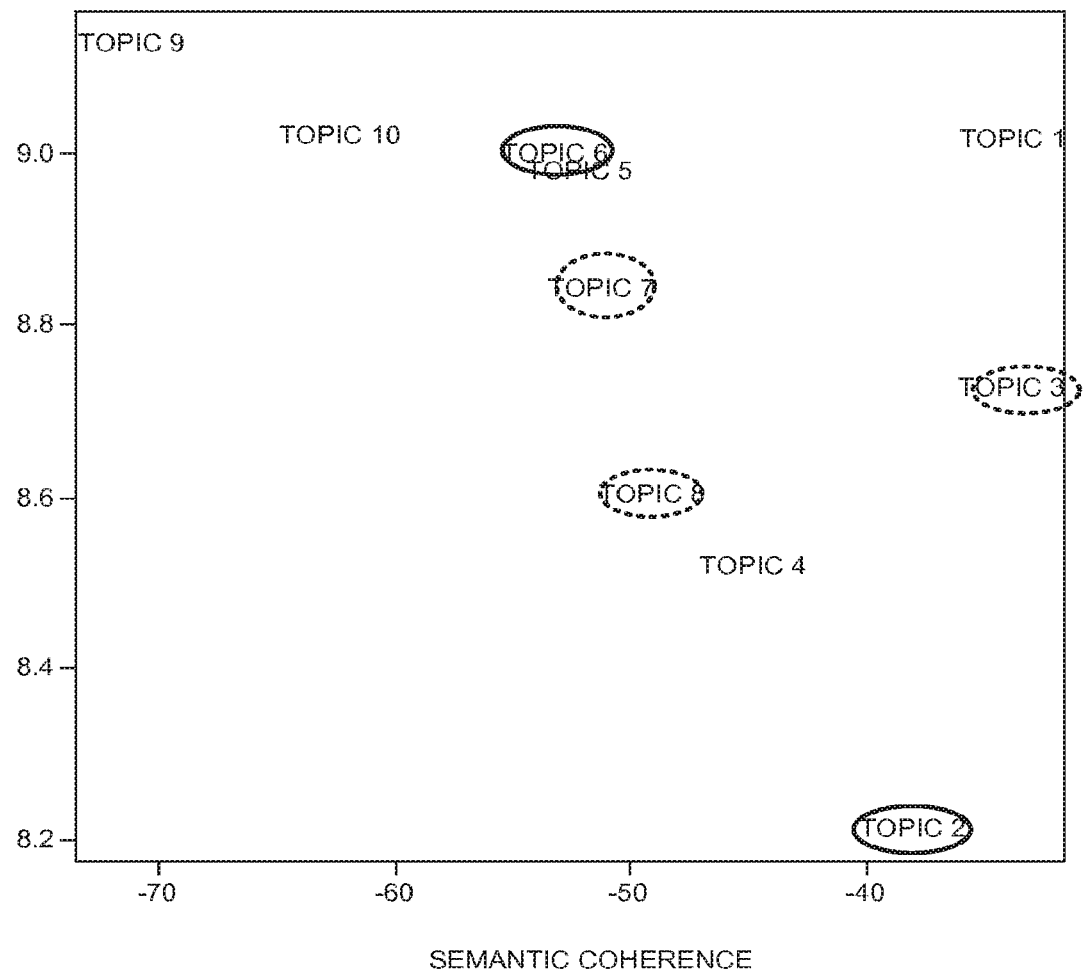
FIG. 8 depicts topic quality metrics associated with ten topics discovered in nursing progress note narrative for in-patients with and without Foley catheters in accordance with an embodiment of the invention.

With reference to FIGS. 3B-8, FIG. 3B depicts example word stems associated with ten topics discovered from the nursing progress note narratives, shown in FIG. 3A, corresponding to patients with and without Foley catheters. FIGS. 4A-4F each depict word-cloud perspective diagrams for topics discovered in unstructured nursing progress note narrative for in-patients with and without Foley catheters. FIG. 5 depicts an example of semantic coherence-exclusivity plot for four top-performing iterations (from among 20 STM runs processing historical/retrospective nursing progress note narrative for in-patients with and without Foley catheters) from among which best model may be selected for use in prediction of conditions prospectively. FIG. 6 depicts one example effect-size plot for ten topics discovered in nursing progress note narrative for in-patients with and without Foley catheters. FIG. 7A depicts an example STM Expectation-Maximization convergence for ten topics discovered in nursing progress note narrative for in-patients with and without Foley catheters. FIG. 8 depicts topic quality metrics associated with ten topics discovered in nursing progress note narrative for in-patients with and without Foley catheters.

Unlike some embodiments of the invention including the example embodiment, other approaches to computer-based diagnostic decision support can only solicit information from the clinician users in a manner that is generic typically because the system is unaware of the current status of the patient or the recent actions and assertions of the user and her/his colleagues, thus forcing the user to enter information or respond to questions whose answers are already present in the EHR. This not only wastes valuable time and impairs usability; it also breaches the user's trust in the system and is psychologically discordant with the notion that the system is designed to help the user in a timely way and behave in manner resembling an intelligent, context-aware human assistant. By contrast, some embodiments of the invention, including the example embodiment reduced to practice, correctly infers membership in a cluster associated with clinically-indicated Foley catheter insertion and seeks responses to a small number of timely and quickly- and easily-answered questions that can buttress the documented evidence substantiating the indicated status and automatically driving further specific recommendations as to genitourinary and skin integrity components of the clinical plan of care, concurrently with the conduct of the care process. Some illustrative example questions for the particular topic or concept of urinary bladder catheterization indications illustratively provided in FIG. 10.

With reference to FIG. 10, some embodiment of the invention may generate a brief query to provide to a caregiver associated with a patient specific in order to confirm or buttress the probability that a patient has a determined condition (which may be determined using method 250). In embodiments, the query may comprise a questionnaire based on the one or more conditions (as indicated by the patient's likely membership in the target classes). For the example embodiment regarding acute Foley catheter clinical insertions described in connection to FIGS. 3A and 3B, such questions may include one or more of the following: (1) Based on recent notes entered by you and/or your colleagues, it appears that this patient has features similar to ones in whom a Foley catheter is indicated. Does this patient have acute urinary retention? (2) Do you expect the patient's urinary output and ability to urinate (in the lavatory or a bedpan) likely to improve in the next 6 to 8 hours such that catheterization would not be indicated? (3) Does the patient have any stage III or IV pressure ulcers in lower back, trunk, buttocks, or hip areas? (4) Does the patient have a severe impairment, which makes positioning or clothing changes uncomfortable for the patient? (5) Does the patient have neurogenic bladder?

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Non-transitory computer-readable media having computer-executable instructions embodied thereon that when executed, facilitate a method for determining one or more patient conditions from unstructured text data, the method comprising:
   receiving a structured topic modeling (STM) model associating terms with metadata labels;
   receiving a set of clusters comprising an association of one or more terms and one or more metadata labels;
   receiving a set of candidate conditions associated with each cluster of the set of clusters based on the association of one or more terms and one or more metadata labels;
   receiving unstructured clinical narratives associated with a particular patient;
   determining, using the STM model and the received unstructured clinical narratives, a likely cluster membership of the particular patient in one or more of a cluster of the set of clusters, wherein the likely cluster membership is determined by calculating a quantitative lexical distance between the unstructured clinical narrative associated with the particular patient and the set of candidate conditions; and
   storing the likely cluster membership of the particular patient in a data store.

2. The media of claim 1, wherein the terms include stemmed terms from a set of historical text documents, and wherein the set of historical text documents comprise unstructured textual clinical narratives associated with the particular patient.

3. The media of claim 2, wherein the unstructured clinical narratives are generated automatically from one or more sensors associated with the particular patient.

4. The media of claim 1, wherein the method further comprises:
   determining, using the clusters, a likelihood of a particular condition, based on the association of one or more terms and one or more metadata labels; and
   determining whether the particular condition is associated with the particular patient based on the determined likelihood and one or more unstructured clinical narratives associated with the particular patient.

5. The media of claim 1, further comprising:
   determining, for each cluster, a listing of conditions, based on the association of one or more terms and one or more metadata labels of the cluster; and
   updating an electronic record to include the listing of likely conditions for the cluster.

6. The media of claim 5, further comprising:
   determining whether each condition in the listing of conditions is associated with the particular patient based on the likely cluster membership of the particular patient and one or more unstructured clinical narratives associated with the particular patient; and
   ranking the listing of conditions according to a likelihood that the particular patient has the condition.

7. The media of claim 6, further comprising providing a notification to a caregiver associated with the particular patient, the notification comprising at least a portion of the listing conditions.

8. The media of claim 6, further comprising generating a set of clinical recommendations for a caregiver associated with the particular patient based on the listing of conditions.

9. The media of claim 8, wherein one or more of the clinical recommendations comprises a suggested clinical order for the patient.

10. The media of claim 6, further comprising generating a set of questions for further assessing the particular patient based on the listing of conditions.

11. The media of claim 10, wherein a number of the set of questions is based on the number of the one or more conditions in the listing, and wherein each question in the set of questions is associated with one or more of the conditions in the listing.

12. The media of claim 1, wherein the set of candidate conditions are determined using the STM model from a corpus of textual records resulting from a care process conducted in a set of prior historical patients.

13. The media of claim 1, wherein records of exemplar members of candidate-condition-associated clusters are determined by calculating a vector cosine of elements denoting a presence, in the clinical narratives associated with the particular patient, of terms extant in clusters of exemplar members.

14. The media of claim 1, wherein records of exemplar members of candidate-condition-associated clusters are determined by the STM model of a historical-patient corpus.

15. The media of claim 1, wherein the STM model determines an identification of a set of top N exemplars including textual content which most strongly embodies statistical association with a condition-labeled cluster.

16. The media of claim 1, further comprising providing a notification to a caregiver associated with the particular patient, the notification comprising the likely cluster membership.

17. The media of claim 1, further comprising generating a set of clinical recommendations for a caregiver associated with the particular patient based on the likely cluster membership.

18. Non-transitory computer-readable media having computer-executable instructions embodied thereon that when executed, facilitate a method for determining one or more likely clinical conditions for a human patient using a structured topic model (STM), the method comprising:
   acquire patient information comprising a set of historical text documents related to care of human patients, each document having metadata labels ascribing one or more conditions of a patient identified at a time the document was created;
   receive a structured topic modeling (STM) model associating terms with metadata labels;
   receive one or more topic-clusters for a candidate condition, each topic-cluster associated with a condition and comprising an association of one or more terms and one or more metadata labels;
   perform K-means clustering on the patient information, using terms in the set of historical text documents and the STM thereby forming a set of patient clusters;
   calculate a lexical distance between each patient cluster and the one or more topic clusters to determine statistical similarity of the patient cluster to the one or more topic clusters;
   for each patient cluster statistically similar to a particular topic cluster, determining that the patient likely has the condition associated with the topic cluster; and
   determining a set of candidate conditions associated with each patient cluster based on the statistical similarity of the patient cluster to the one or more topic clusters;
   updating the patient information to indicate that the patient has a likelihood of having the condition;
   receiving unstructured clinical narratives associated with a particular patient;
   determining, using the STM model and the received unstructured clinical narratives, a likely cluster membership of the particular patient into one or more of the topic clusters, wherein the likely cluster membership is determined by calculating a quantitative lexical distance between the unstructured clinical narratives associated with the patient and the set of candidate conditions; and
   updating the unstructured clinical narrative to indicate the likely cluster membership of the particular patient.

19. The media of claim 16, further comprising determining a health care software routine for providing care plan for the condition for the patient and modifying the software routine according to a likelihood of the patient having the condition.

20. A method for determining one or more patient conditions from unstructured text data, the method comprising:
   acquiring a set of historical text documents related to care of human patients, each document having metadata labels ascribing one or more conditions of a patient associated with the document, the one or more conditions identified at a time the document was created;
   receiving a structured topic modeling (STM) model associating terms with metadata labels;
   receiving a set of clusters comprising an association of one or more terms and one or more metadata labels;
   determining, for each cluster, a listing of conditions, based on the association of one or more terms and one or more metadata labels of the cluster;
   receiving unstructured clinical narratives associated with a particular patient;
   determining using the STM model and the received unstructured clinical narratives, a likely cluster membership is determined by calculating a quantitative lexical distance between the unstructured clinical narratives associated with the particular patient and the listing of conditions; and
   storing an electronic record of the likely cluster membership of the particular patient in the data store.

* * * * *